US00PP28903P2

(12) United States Plant Patent
Hansen

(10) Patent No.: US PP28,903 P2
(45) Date of Patent: Jan. 30, 2018

(54) ***BUDDLEIA* PLANT NAMED 'PRINCE CHARMING'**

(50) Latin Name: *Buddleia davidii*
Varietal Denomination: Prince Charming

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 15/530,090

(22) Filed: Dec. 1, 2016

(51) Int. Cl.
*A01H 5/02* (2006.01)

(52) U.S. Cl.
USPC ..... Plt./242

(58) Field of Classification Search
USPC ..... Plt./242
CPC ..... A01H 5/00; A01H 5/02
See application file for complete search history.

*Primary Examiner* — Kent L Bell

(57) ABSTRACT

*Buddleia* 'Prince Charming' is a short, compact, mounded, multi-stemmed, winter-hardy butterfly bush with long, compact, flowering, thyrse over a long season beginning mid-summer with sweetly-fragrant flowers of bright cerise-pink to raspberry-pink petals that are attractively offset by dark green foliage with silvery undersides. The new plant is valuable for landscaping en masse, as an accent or as a potted specimen.

1 Drawing Sheet

Botanical classification: *Buddleia davidii.*
Variety denomination: 'Prince Charming'.

BACKGROUND OF THE PLANT

The present invention relates to the new and distinct butterfly bush plant of the Scrophulariaceae family, *Buddleia* 'Prince Charming' hybridized by Hans A. Hansen in the summer of 2013 at a wholesale perennial nursery in Zeeland, Mich., USA. 'Prince Charming' is the result of an ongoing breeding program conducted by the inventor. The goals for this program have been to produce improved, garden-worthy plants for the ornamental plant market. The new plant, originally assigned breeder code 13-10-2, is a single seedling selection from a cross between the unreleased proprietary hybrid 12-67-01 (not patented) as the female or seed patent. The male parent was from an isolation block of unreleased proprietary siblings to the proprietary hybrid 12-67-01 and may have been a sibling of 12-67-01 or a selfing. The new cultivar was discovered and selected as an individual flowering plant within the progeny of the above stated cross-pollination during the summer 2013 in a controlled environment at the same nursery in Zeeland, Mich.

No plants of *Buddleia* 'Prince Charming' have been sold, under this or any other name, in this country or anywhere in the world, prior to the filing of this application, nor has any disclosure of the new plant been made prior to the filing of this application with the exception of that which may have been disclosed within one year of the filing date of this application and was either derived directly or indirectly from the inventor.

*Buddleia* 'Prince Charming' was first asexually propagated from a single select plant in 2015 by stem cuttings at the same nursery in Zeeland, Mich. The resultant asexually propagated plants have been found to be stable and true to type in successive generations of asexual reproduction.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

Compared to the female plant the new plant has a deeper cerise-pink to raspberry-pink flower color and is less sprawling in habit. Comparison to the male plant is not possible as the exact male plant is not known.

The nearest comparison plants are *Buddleia* 'Miss Molly' U.S. Plant Pat. No. 23,425, and 'Miss Ruby' U.S. Plant Pat. No. 19,950, 'Red Chip' (not patented), Pink Pagoda' U.S. Plant Pat. No. 23,214, 'Pink Micro Chip' U.S. Plant Pat. No. 26,547 and 'Queen of Hearts' U.S. Plant Pat. No. 27,987. 'Miss Molly', 'Miss Ruby', 'Red Chip' and 'Queen of Hearts' are all taller and wider in habit than 'Prince Charming'. 'Prince Charming' is more compact in branching, height and width with flowers having a more bright cerise-pink to raspberry-pink coloration than all of the above butterfly bush cultivars.

*Buddleia* 'Prince Charming' is a unique winter-hardy butterfly bush different from all other *Buddleia* cultivars known to the inventor based on the following combined repeatedly observed distinguishing traits:

1. Winter-hardy butterfly bush shrub, with multiple-stemmed, branched, compact, rounded-mounded habit.
2. Many-flowered compact thyrse over a prolonged season beginning mid-summer.
3. Flowers with bright cerise-pink to raspberry-pink petals.
4. Lanceolate foliage of dark green with silvery undersides.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
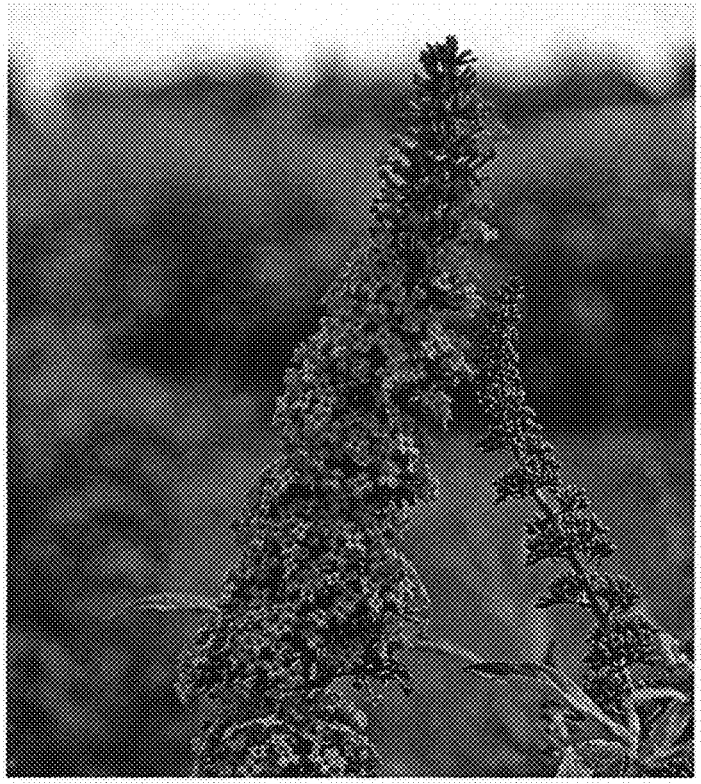
FIG. 1 shows a close-up of the inflorescence.
Figure 2:
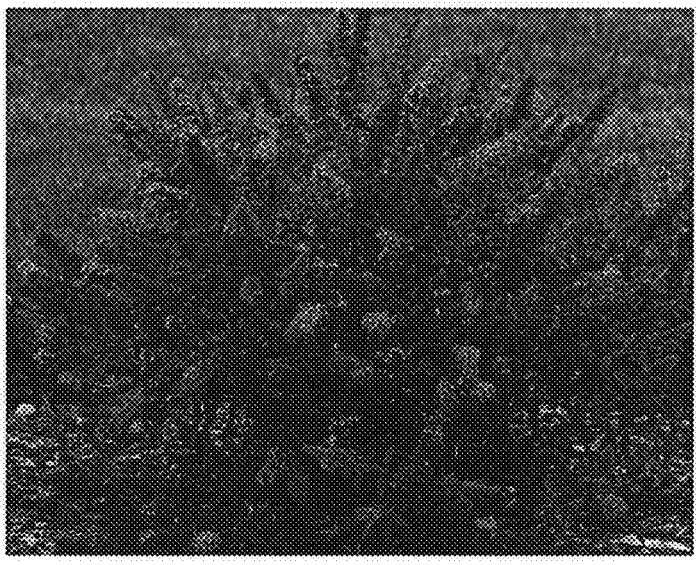
FIG. 2 shows the habit of a three-year-old plant in mid-season flowering.

The following descriptions and color references are based on the 2001 edition of The Royal Horticultural Society Colour Chart except where common dictionary terms are used. The new plant, *Buddleia* 'Prince Charming', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand, open-sun, field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in early spring.

Parentage: Unreleased proprietary hybrid 12-67-01 (not patented) as the female or seed patent; unreleased proprietary siblings to the proprietary hybrid 12-67-01 as the male or pollen parent.

Propagation:

*Method.*—Softwood cuttings.

*Time to initiate roots from tissue culture.*—About two weeks.

*Rooting habit.*—Normal, dense and branching, developing thick at base to about 1.5 cm diameter.

*Root color.*—Creamy white between RHS 159A and lighter than RHS 159 D depending on soil type.

*Crop time.*—Under normal summer growing conditions 12 to 15 weeks to flower in a four-liter container from cutting. Plant vigor is very good.

Plant description:

*Plant shape and habit.*—Winter-hardy, herbaceous to semi-woody, well-branched shrub with about 14 thick upright and branched main stems producing a compact rounded mound about 90 cm tall and about 117 cm wide.

*Stem.*—Terete and woody in lower portion, with exfoliating bark; younger upper portion puberulent; strong and flexible; average about 75 cm tall from soil line to just below terminal flowers, and about 0.8 cm diameter at the base; before distal flowers about 12 branches per main stem in upper six nodes, extending at about 45° angle from horizontal.

*Stem color.*—Distal portion just below flowers between RHS 146D and RHS 147D with tinting of nearest RHS 61B in regions of high light exposure; basal 10 cm between RHS 200C and RHS 165B with striations between RHS 200A and RHS N199B.

*Internode.*—About 10 nodes per main stem below flowers, average internode length about 7.5 cm on unpinched plant; upper internodes slightly more elongated than lower internodes.

Foliage description: Opposite, decussate; serrate; puberulent to pulverulent abaxial and glabrous adaxial; elliptic; attenuate to cuneate base and acute apex; sessile; no foliar fragrance detected.

*Leaf blade size.*—Up to about 6.1 cm long and about 19.0 mm wide, average about 5.5 cm long and about 16.0 mm wide; becoming smaller in distal portion of stem.

*Foliage color.*—Young expanding leaf adaxial side nearest RHS 144A, young expanding abaxial nearest RHS 149D; mature leaves adaxial side between RHS 139A and RHS 137A, mature abaxial nearest RHS 194A.

*Veins.*—Reticulate; abaxial costate, puberulent to pulverulent; adaxial glabrous, slightly impressed.

*Vein color.*—Abaxial midrib nearest RHS 147C and secondary veins nearest RHS 194A; adaxial midrib nearest RHS 195B and secondary veins between RHS 139A and RHS 137A.

*Petioles.*—Leaves sessile.

*Inflorescence description.*—Glomerate thyrse consisting of about 400 persistent salverform flowers; to about 15.0 cm long and about 4.5 cm across; beginning in mid-July and continuing until frost in Michigan.

*Buds.*—Elongated clavate, apex rounded; one day prior to opening about 10.0 mm long and about 2.5 mm diameter in club and throat about 1.0 mm diameter in throat and about 8.0 mm long.

*Bud color.*—Nearest RHS 64A in club portion, basal one-third of tube portion nearest RHS 2D, distal two-thirds of tube nearest RHS 53C.

*Sepals.*—Typically four, proximal two-thirds connate, adpressed to corolla tube; acute apex; glabrous adaxial and pubescent abaxial; margin entire; fused in about the basal 1.6 mm and split in about the terminal 0.9 mm; forming a corolla about 2.5 mm long and about 1.0 mm across; individually less than about 1.0 mm wide at point of fusion.

*Sepal color.*—Adaxial and abaxial nearest RHS 138A along center longitudinal axis and nearest RHS 138D along margins of abaxial and adaxial.

*Flowers fragrance.*—Pleasantly and distinctly sweet.

*Petals.*—Four; glabrous; fused into salverform with typically straight terete tube about 9.0 mm long and 1.0 mm diameter, and a abruptly applanate face about 7.0 mm across; petal blade rounded with crenate margin; apex rounded; blade to about 2.5 mm across and about 3.0 mm long from fused face.

*Petal color.*—Adaxial tube base nearest RHS 2D, distal one half tube center nearest RHS 171B, adaxial face blades between RHS 71B and RHS 71C when first open and lightening to nearest RHS 71D with age; abaxial tube base nearest RHS 2D, distal two-thirds of tube nearest RHS 53C and abaxial petal blades between RHS 71B and RHS 71C when first open and lightening to nearest RHS 71D with age.

*Gynoecium.*—Pistil: one; about 3.2 mm long; Style: short, round, glabrous; about 1.2 mm long and less than 0.2 mm diameter; color nearest RHS 145D; Stigma: oblong, minutely puberulent; about 0.2 mm in diameter and about 0.5 mm long; color nearest RHS 144B; Ovary: superior; oblong globose; about 1.0 mm across at base and 1.5 mm tall; distally tapering to style; color nearest RHS 145A.

*Androecium.*—Four; Filaments: not produced or very short; Anthers: typically four; oblong; introrse; adnate to about mid-point of corolla tube; about 1.0 mm long and 0.5 mm wide; color nearest RHS 18B; Pollen: globose, less than 0.1 mm long; color nearest RHS 18B.

*Pedicel*.—Short, puberulent; about 1.0 mm long and about 0.5 mm diameter; color nearest than RHS N138B.

*Peduncle*.—Quadrangular, puberulent to pulverulent, flexible and strong; to about 17.0 cm long, and about 1.5 mm diameter at base below flowers.

*Peduncle color*.—Between RHS 146D with less direct light and RHS 147D with tinting of nearest RHS 187A in more intense light.

*Fruit*.—Moderate fruit set; oblong with acute apex; glabrous, bi-valved, septicidal capsule; about 5.0 mm long and about 1.7 mm diameter.

*Fruit color*.—As maturing nearest RHS 162D; when mature and dehiscing nearest RHS 164B.

*Seed*.—Elongated linear with sharply acute ends; about 1.5 mm long and less than 0.2 mm across in center.

*Seed color*.—Nearest RHS 200A.

Disease resistance: Resistance has been noted to deer browsing. Other resistance beyond that common to butterfly bush cultivars has not been observed. The plant grows best with plenty of moisture and adequate drainage, but is able to tolerate some drought when mature. Hardiness at least from USDA zone 6 through 10.

It is claimed:

1. A new cultivar of winter-hardy butterfly bush *Buddleia* plant named 'Prince Charming' as herein illustrated and described.

* * * * *